United States Patent
Pothuri et al.

(10) Patent No.: US 6,712,972 B2
(45) Date of Patent: Mar. 30, 2004

(54) METHOD FOR THE SYNTHESIS AND EVALUATION OF PORPHYRINS, CALIX (4) PYRROLES AND ALLIED MACROCYCLES

(75) Inventors: Sita Devi Pothuri, Andhra Pradesh (IN); Kondapuram Vijaya Raghavan, Andhra Pradesh (IN); Shivanand Janardan Kulkarni, Andhra Pradesh (IN); Radha Kishan Motkuri, Andhra Pradesh (IN); Radha Rani Vippagunta, Andhra Pradesh (IN); Mamidanna Rama Venkata Satyanarayana Murty, Andhra Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 35 days.

(21) Appl. No.: 10/113,210

(22) Filed: Mar. 28, 2002

(65) Prior Publication Data

US 2003/0183577 A1 Oct. 2, 2003

(51) Int. Cl.$^7$ ................................................ B01D 15/08
(52) U.S. Cl. ................ 210/658; 210/198.3; 204/157.72; 540/145
(58) Field of Search .............................. 210/658, 198.3; 204/157.72; 436/162; 540/145

(56) References Cited

U.S. PATENT DOCUMENTS 3,702,886 A 11/1972 Argauer et al. ............. 423/328

6,605,194 B2 * 8/2003 Raghavan et al. ..... 204/157.72

FOREIGN PATENT DOCUMENTS

WO    WO 97/37995    10/1997    ............ 204/157.72

OTHER PUBLICATIONS

A. Petit et al., *Synthetic communication*, 1992, 22(8) 1137–1142.
C.T. Kresge et al., *Nature*, 1992, 359:710–712.
M. Grün et al., *J. Chromatography A*, 1996, 740(1):1–9.
Lorenzo Williams, *Chem Commun.*, 2000, 435–436.
Manas Chakrabarty et al., *Tetrahedron Letters*, 2001, 42:3913–3915.
PCT Search Report.
M. Radha Kishan et al., *Chem. Commun.*, 2001, 2226–2227.

* cited by examiner

*Primary Examiner*—Ernest G. Therkorn
(74) *Attorney, Agent, or Firm*—Morgan & finnegan, LLP

(57) ABSTRACT

The present invention provides an innovative method based on reaction cum separation on single plate concept for efficient evaluation of porphyrins, calix(4)pyrroles and allied macrocycles by in-situ synthesis from pyrrole with aromatic aldehydes and ketones over zeolite based molecular sieve catalysts as sorbents in thin layer chromatography (TLC) using microwave heating. This glass backed zeolite coated TLC plate acts as a micro reactor as well as separator for the in-situ synthesis and chromatographic separation of macrocycles. The process is simple, economical, rapid, selective and finds a possible application in high throughput parallel synthesis and screening on a single micro plate employing microwave irradiation.

12 Claims, No Drawings

METHOD FOR THE SYNTHESIS AND EVALUATION OF PORPHYRINS, CALIX (4) PYRROLES AND ALLIED MACROCYCLES

FIELD OF THE INVENTION

The present invention relates to a method for the in-situ synthesis and screening of tetra-arylporphyrins, meso-octamethyl calix(4)pyrroles and allied macrocycles by reacting pyrrole and corresponding aldehydes and ketones using a specific zeolite based molecular sieve catalyst as sorbent in thin layer chromatography under microwave irradiation. In particular, the present invention provides new opportunities for parallel synthesis and screening on a single plate for producing tetraphenyl porphyrins by reacting pyrrole with benzaldehyde and calix(4)pyrroles from pyrrole and acetone in presence of zeolites and MCM-41 molecular sieves as sorbents in TLC under microwave irradiation with an online spectroscopic evidence.

The process of the invention leads to efficient and quantitative method for the screening of the selective catalytic activity of a zeolite catalyst as sorbents in TLC for in-situ synthesis of tetraaryl porphyrins, calix(4)pyrroles and allied macrocycles. The zeolite based TLC plays the role of a microreactor cum separator exemplified by rapid processing for possible applications to combinatorial chemistry.

BACKGROUND OF THE INVENTION

In recent years, significant effort has been directed towards the design and synthesis of macrocycles such as porphyrins and calix(4)pyrroles over mesoporous molecular sieves. Among the various macrocycles, extensive research in the area of synthesis, characterization and utilization of porphyrins and calixpyrroles is in progress. Synthesis of Porphyrin and Calix(4)pyrrole compounds as well as methods for synthesising the same are well recognised in the art. Porphyrins are conjugated macrocyclic species composed of four pyrrole rings linked to the position via $sp^2$ hybridized carbon atoms. However porphyrin and pyrrole compounds are expensive. For example, porphyrin is offered at costs as high as \$15,000/g. Even though a great variety of catalysts like organic and inorganic acid catalysed syntheses are reported they suffer from the reusability of the catalyst and poor yields. Further, the impure corroles formation makes the separation of the pure compound difficult. The first such report of synthesis of porphyrin molecules under microwave irradiation by A. Petit et al (*Synthetic Communication* 22(8) (1992) 1139) by employing silica alumina, clay and montmorillonite as a catalyst is popular but it suffers from poor yields (not more than 10%).

Calix(4)pyrroles represent a class of macrocycles, which are non-conjugated macrocyclic species composed of four pyrrole rings linked to the position via $sp^3$ hybridized carbon atoms. Calixpyrroles that carry meso-hydrogen atoms are prone to oxidation to the corresponding porphyrins. Recently we have reported the synthesis of these Calix(4)pyrroles over zeolites and mesoporous MCM-41 molecular sieves with good yields and selectivities, which is an eco-friendly and environmentally clean process (*Chem. Commun.* 2001, 2226). Such macrocycles have unusual properties that make them particularly useful. Calixpyrroles bind anion and neutral molecular species in solution and in the solid state in such an effective and selective way the anions or neutral molecular species can be separated from other anions and neutral molecular species. Further the affinity a macrocycle has for a particular species can be 'tuned' by strategic choice of electron-donating or electron-withdrawing peripheral substituents for the synthesis of macrocycles.

According to WO 97/37995, various types of calixpyrroles was synthesized using different ketones. Application of these macrocycles for removal of biological ions or neutral molecule species for clinical use, removal of undesirable ions or neutral molecule species from environmental sources provides only a few of the practical and important uses. These calix(4)pyrroles can be used in the dialysis of bodily fluids. Examples of dialyzable substrutex include, but are not limited to phosphate containing molecules or halide waste (i.e. diabetes or drug overdoses and kidney dialysis).

Since these macrocycles, viz., porphyrins and calix(4) pyrroles are important moieties in host-guest chemistry as drug transporting agents, their synthesis demands an eco-friendly, clean, economical and free handling process.

Porous materials created by nature or by synthesis have found great utility in all aspects of human activity. The pore structure of solids is usually formed in the stages of crystallization or subsequent treatment. Depending on their predominant pore size, the solid materials are classified as microporous, mesoporous and macroporous materials. The only class of porous materials possessing rigorously uniform pore sizes is that of Zeolites and related molecular sieves. Zeolites are uniform porous crystalline aluminosilicates and their lattice is composed by $TO_4$ tetrahedra (T=Al and Si) linked by sharing the apical oxygen atoms (D. W. Breck, *Zeolite molecular sieves: Structure, Chemistry and Use*; Wiley and Sons; London 1974). But due to the smaller pore size of zeolite molecular sieves restricted their wide range applications, especially in synthesis of macrocycles. However, this has been overcome by the report of Mesoporous molecular sieves by Mobil researchers (C. T. Kresge, M. E. Leonowicz, W. J. Roth, J. C. Vartuli and J. S. Beck, *Nature* 359 (1992) 710) in 1992. These Mesoporous molecular sieve (MCM-41) has been opened a new era in the zeolite catalysis. Many reports have been published on the applications of this material for the catalytic activity towards oxidation, acylation, alkylation and cyclization. They are the support materials for enzymes, whole cell immobilization and nano particles. Their potentiality, due to organized pore structure with large surface area, has stimulated research in different fields of application among which catalysis, adsorption and chromatography are the most interesting ones. The first usage of mesoporous silica and aluminosilicate as stationary phases was reported by Grun et al, which prepared MCM-41 material in alkaline medium from cationic surfactants (*J. Chromatography* A 740, 1, 1996). Recent reports utilized the technique of silica gel thin layer chromatography (TLC) and microwave irradiation as a tool for reaction optimization. (*Chem. Commun* 2000, 435; *Tetrahedron Letters* 42, 2001, 3913). However, the method is limited to synthesis of simple molecules.

OBJECTS OF THE INVENTION

The main object of the present invention is to provide a process for the in-situ synthesis and evaluation of porphyrins such as meso-tetraphenyl porphyrin over zeolite and MCM-41 molecular sieves coated TLC plates under microwave conditions, where in a fast, eco-friendly heterogeneous catalytic process could be accomplished.

Another object of the present invention is to provide a process for the in-situ synthesis and evolution of calix(4) pyrroles such as meso-octamethyl calix(4)pyrrole over zeolite and MCM-41 molecular sieves coated TLC plates under microwave conditions, where in a fast, eco-friendly heterogeneous catalytic process could be accomplished.

Still another object of the present invention is in-situ synthesis of porphyrins, calix(4)pyrroles and allied macrocycles over molecular sieves coated TLC plates with microwave assisted reaction.

SUMMARY OF THE INVENTION

The present invention relates to a the use of zeolites and mesoporous MCM-41 as stationary phases in TLC, for a rapid, in-situ synthesis, identification and quantification of Porphyrins, Calix(4)pyrroles and allied macrocycles using the combinatorial approach to identify and estimate the yield of product. The present invention provides an in-situ synthesis of porphyrins and calix(4)pyrrole compounds and their simultaneous screening over solid acid catalysts. It provides new opportunities for the combinatorial approach for the rapid screening of macrocycles.

Accordingly, the present invention provides a method for high performance. Thin Layer Chromatography (TLC) and microwave assisted in-situ synthesis and evaluation of a tetraphenyl porphyrin comprising reacting the corresponding pyrrole and an aromatic aldehyde, on a glass backed zeolite catalyst coated TLC plate.

In one embodiment of the invention, the zeolite is coated onto the TLC plate using a binder selected from the group consisting of calcium sulfate, gypsum, starch and cellulose.

In another embodiment of the invention, the catalyst used is selected from the group consisting of Al-MCM-41, HZSM-5, Hβ, HX, synthetically prepared SAPO-5 and HY.

In another embodiment of the invention, the zeolite used is in its alkali ion form wherein the alkali ion is selected from the group comprising sodium and potassium, ammonium ion form or proton form.

In another embodiment of the invention, the aromatic aldehyde is selected from the group consisting of benzaldehyde, o, m and p-substituted benzaldehydes.

In another embodiment of the invention, the process comprises the in situ synthesis and characterization of meso-tetraphenyl porphyrin of formula 1

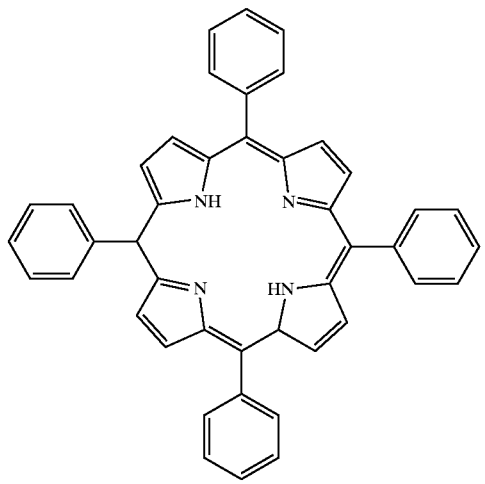

from corresponding pyrrole and benzaldehyde over mesoporous and microporous molecular sieves as stationary phases on inert glass backed supports in solvent free microwave heating.

The present invention also relates to a method for the high performance Thin Layer Chromatography (TLC) and microwave assisted in-situ synthesis and evaluation of meso-octamethyl calix(4)pyrrole comprising reacting the corresponding pyrrole and ketone over a glass backed zeolite coated TLC plate.

In one embodiment of the invention, the catalyst used is selected from the group consisting of Al-MCM-41, HZSM-5, Hβ, HX, synthetically prepared SAPO-5 and HY.

In another embodiment of the invention, the ketone is selected from the group consisting of acetone, methyl ethyl ketone, diethyl ketone, cyclopentanone, cyclohexanone, cycloheptanone, cyclooctanone, cyclododecanone, substituted cyclohexanones, acetophenone and alkyl and aryl derivatives thereof.

In one embodiment of the invention, the zeolite is coated onto the TLC plate using a binder selected from the group consisting of calcium sulfate, gypsum starch and cellulose.

In another embodiment of the invention, the zeolite used is in its alkali ion form wherein the alkali ion is selected from the group comprising sodium and potassium, ammonium ion form or proton form.

In another embodiment of the invention, the process comprises the facile and in situ synthesis of a meso-octamethyl calix(4)pyrrole of the formula 2

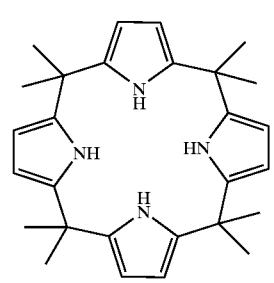

from the corresponding pyrrole and acetone over mesoporous and microporous molecular sieves as stationary phases on inert glass backed supports in solvent free microwave heating.

DETAILED DESCRIPTION OF THE INVENTION

The present invention provides an improved process that comprises a combinatorial approach with environmentally clean technology, low wastage, less cumbersome, very fast, easily separable method with an online spectroscopic screening facility.

The catalyst used in this process is easily coated on the glass backed TLC plate with a help of a binder. The zeolite support used acts as a micro reactor type stationary phase and also as an acid catalyst. The method provides a reaction, which is accelerated by microwave irradiation, development and evaluation by online spectroscopic data in a combinatorial approach. The present invention relates to novel method for in-situ synthesis of tetraphenyl porphyrins by reacting pyrrole with aromatic aldehyde over zeolite backed TLC plates under microwave irradiation, where in the catalyst could be obtained by commercial outlet or by synthesis. The aromatic aldehydes used in the present invention include, benzaldehyde, o, m and p-substituted benzaldehydes and a plethora of aliphatic aldehydes. Representative examples of ketones include, acetone, methyl ethyl ketone, diethyl ketone, cyclopentanone, cyclohexanone, cycloheptanone, cyclooctanone, cyclododecanone, substituted cyclohexanones, acetophenone and alkyl and aryl derivatives thereof. The molecular sieves used in the present invention include commercially available HZSM-5, HY, Hβ, HX, and synthetically prepared SAPO-5 and mesoporous MCM-41. For example, zeolites of HZSM-5 series are available from Conteka, Sweden, HY and Hβ from PQ corporation USA. The methods for producing them are described in detail in U.S. Pat. No. 3,702,886 (ZSM-5). Furthermore, MCM-41 (C. T. Kresge, M. E. Leonowicz, W. J. Roth, J. C. Vartuli and J. S. Beck, Nature 359 (1992) is synthesized by an aqueous solution of aluminum isopropoxide (0.76 g) to which an aqueous solution of sodium hydroxide (0.3 g) was added in 50 ml beaker and stirred in hot conditions, till a clear solution was formed. Now, to the above mixture 9.4 ml of tetraethyl ammonium hydroxide (TEAOH) is added under cooling conditions. Tetraethyl orthosilicate (23.4 ml) (TEOSi) was dissolved in 50 ml of water in another 250 ml beaker separately and allowed to stirring at room temperature for 30 minutes. Solution of TEAOH, NaOH mixture was then added dropwise to TEOSi with constant stirring. Subsequently, hexadecyl trimethyl ammonium bromide (10.55 g) was added slowly to the above solution. Maintaining the pH of the mixture at 11.0–11.5. Finally, the gel mixture was transferred into an autoclave and heated at 100° C. for 24 h. Solid product was recovered by filtration, washed with deionized water and dried in air. All as-synthesized samples were calcined at 773K in air. The obtained Al-MCM-41 catalyst was modified with 1% ammonium nitrate.

The zeolite used in the present invention may be of any alkali ion form such as sodium, potassium or the like, ammonium ion form or proton form The alkali ion, however, is not preferred because it lowers the catalytic activity if it remains in the catalyst till the end. The microwave power varied from low to high power and the time of heating also varied from 3 minutes to 25 minutes. The binder used for the zeolite coating on the glass plate includes $CaSO_4.2H_2O$, gypsum, starch and cellulose. The present study attempts to employ microporous zeolites and mesoporous MCM-41 mesoporous sieves as sorbents in thin layer chromatography. The micropores range from 5–15 Å and mesopores range from 20–50 Å. The glass plates are used as solid support and the molecular sieves are coated on the plate as matrix with the help of Calcium sulfate as a binder. The plates are subsequently dried in oven at 110° C. for 45 min and cooled. The reactants are applied on the plates with help of a micro syringe using Linomat IV (CAMAG-HPTLC) with nitrogen gas as application device. The reactants are dissolved in suitable solvents such as chloroform in the case of porphyrin synthesis and dichloromethane in calixpyrrole synthesis prior to application.

In-Situ Synthesis of Porphyrins Over TLC

Equimolar ratio of reactants, pyrrole and benzaldehyde are dissolved in 5 ml of chloroform and applied on zeolite coated TLC plates. On each plate, 30 µl of reactant mixture is applied as first track and irradiated in domestic microwave oven (BPL) for 12 min with 2 min interval of time. After irradiation, 5 µl of authentic (meso-tetraphenyl porphyrin) sample is applied as second track. The plate was subsequently developed in a twin trough chamber using chloroform and methanol (9.5:0.5). The plate is now densitometrically scanned using scanner (CAMAG TLC scanner 3) under absorption/reflection mode at 254 nm (deuterium lamp). Further, the plate is also scanned from 350 to 650 nm under spectrum mode to evaluate the soret band of the porphyrin at 419 nm along with the Q-band at 515, 598 and 647 nm. The percentage composition has been obtained from the densitogram complemented by the characteristic spectra. When HZSM-5 coated TLC plate was used, because of its high acidic nature, formation of the porphyrin is observed but selectivity is less. It may be due to the low porosity (5.6 Å) of the zeolite, wherein only the surface reaction has been facilitated. When Hβ was used as catalyst, low sensitivity of the cyclized product, has been observed with low conversion of pyrrole, while HY coated TLC plates did not facilitate the reaction to occur. It has been indicated by the profile of chromatogram.

In-Situ Synthesis of Calix(4)Pyrroles Over TLC

Similarly, equi molar ratio of reactants, ie., pyrrole and acetone are dissolved in 5 ml of dichloromethane and applied on zeolite coated TLC plates. On each plate, 30 µl of reactant mixture has been applied as fir track and irradiated in domestic microwave oven for 3 min. The irradiation time varied from 3 min to 5 min. After irradiation, 5 µl of authentic (meso-octamethyl calix(4)pyrrole) sample is applied as second track. The plate is subsequently developed in twin trough chamber using chloroform and methanol and air dried. The plate is now densitometrically scanned using scanner (CAMAG TLC scanner 3) under absorption/reflection mode at 254 nm (deuterium lamp). The percentage composition is obtained from the densitogram complemented by the characteristic spectra. Pore size, acidity and surface area of the all the zeolite molecular sieve catalysts played a major role in these reactions. All the catalysts were characterized by X-ray diffraction, Infrared spectroscopy, BET-surface area and $NH_3$-Temperature programmed desorption. The inventors found that the calcium sulfate was better binder than other binders like starch and cellulose.

The process of this invention is described in further detail below by the following examples, which are illustrative and are not intended to limit the scope of this invention.

EXAMPLE 1

Coating of Zeolites on Glass Plates:

40 mg of the binder ($CaSO_4.2H_2O$, $CaSO_4.1/2H_2O$ or starch) is taken in 8–10 ml of boiling water and maintained at boiling condition for 10 min. 2 g each of the zeolite (HZSM-5, Hβ, HY) or mesoporous molecular sieve (MCM-41) was added to the boiling solution of the binder and mixed vigorously for one minute. The gel was applied in hot condition uniformly on to the glass plates (2.5×7.5) as thin layers. The plates were further air dried for 30 min, oven dried at 110° C. for 1 h and cooled in a desiccater.

EXAMPLE 2

In-situ synthesis and evaluation of meso-tetra phenyl porphyrin: The equi molar ratio of reactants, pyrrole (0.1 ml) and benzaldehyde (0.15 ml) were dissolved in 5 ml of chloroform and applied on Al-MCM-41 coated TLC plates (2.5×7.5 mm). On each plate, 30 µl of reactant mixture is applied as first track and irradiated in domestic microwave oven (BPL) for 12 min with 2 min interval of time. The irradiation time varied from 3 min to 25 min. After irradiation, 5 µl of authentic (meso-tetraphenyl porphyrin) sample is applied as second track. The plate was subsequently developed in twin trough chamber using chloroform and methanol (9.5:0.5). The plate is now densitometrically scanned using scanner (CAMAG TLC scanner 3) under absorption/reflection mode at 254 nm (deuterium lamp). Parameters, plate width, start position, band, space are input to the software and integrated. Further, the plate is also scanned from 350 to 650 nm under spectrum mode to evaluate the soret band of the porphyrin at 419 nm. Percentage composition is obtained from the densitogram complemented by the characteristic spectra. Yield of the corresponding meso-tetraphenyl porphyrin is about 56.5% (±10% deviation in all the cases studied). In a separate analysis, after scanning the TLC plate, corresponding peak of porphyrin is scrapped and extracted out using chloroform as solvent. Crystals remaining upon evaporation of solvent were subjected to FAB-MS. m/z at 615 which is vividly noticed confirmed the authentic identification of porphyrins. This is in support of the soret band observed at around 419 nm in UV spectrum Matrix effect on UV range is always noticed with a bathochromic shift.

EXAMPLE 3

The reaction is carried out in same manner as in example 2 over HZSM-5 coated TLC plate and the yield of tetraphenyl porphyrin is 50.4% (±10% deviation).

EXAMPLE 4

The reaction is carried out in same manner as in example 2 over Hβ coated TLC plate catalyst, the conversion to porphyrin was not noticed because the corresponding UV spectrum or the chromatogram was not obtained.

EXAMPLE 5

Similarly, when the reaction is carried out in same manner as in example 2 over HY coated TLC plate, the catalyst failed to facilitate the porphyrin formation perhaps due to low pore size of sodalite cage.

EXAMPLE 6
In-Situ Synthesis and Evaluation of meso-octamethyl calix (4)pyrrole

Equimolar ratio of reactants, pyrrole (0.1 ml) and acetone (0.1 ml) were dissolved in 5 ml of dichloromethane and applied on Al-MCM-41 coated TLC plates (2.5×7.5 mm). On each plate, 30 μl of reactant mixture is applied as first track and irradiated in domestic microwave oven at a power of 2450 MHz (BPL) for 3 min. The irradiation time varied from 3 min to 5 min. After irradiation, 5 μl of authentic meso-octamethyl calix(4)pyrrole sample is applied as second track. The plate was subsequently developed in twin trough chamber using chloroform and methanol (9.5:0.5). The plate is now densitometrically scanned using scanner (CAMAG TLC scanner 3) under absorption/reflection mode at 254 nm (deuterium lamp). The parameters, plate width, start position, band, space are input to the software and integrated. The percentage composition is obtained from the densitogram complemented by the characteristic spectra. The yield of the corresponding meso-octamethyl calix(4) pyrrole was observed as 79.1% (±10% deviation in all the studies carried out). After scanning the TLC plate, the corresponding peak of calixpyrrole is scrapped and extracted out using the DCM solvent, which is then subjected to EI-MS and m/z of 428 is observed. HR-MS(EI): for calcd for $C_{28}H_{36}N_4$: calcd: 428.2939; found: 428.2938.

EXAMPLE 7

The reaction is carried out in same manner as in example 6 over HZSM-5 coated TLC plate and the yield of meso-octamethyl calix(4)pyrrole is 58.2%.

EXAMPLE 8

The reaction is carried out in same manner as in example 6 over Hβ coated TLC plate and the yield of meso-octamethyl calix(4)pyrrole is 65.3%.

EXAMPLE 9

Similarly, when the reaction is carried out in same manner as in example 6 over HY coated TLC plate, the pore size has been restricted the formation of meso-octamethyl calix(4) pyrrole of the formula 2 given above.

We claim:
1. A method for high performance Thin Layer Chromatography (TLC) and microwave assisted in-situ synthesis and evaluation of a tetraphenyl porphyrin comprising reacting the corresponding pyrrole and an aromatic aldehyde, on a glass backed zeolite catalyst coated TLC plate.

2. A method as claimed in claim 1 wherein the zeolite is coated onto the TLC plate using a binder selected from the group consisting of calcium sulfate, gypsum, starch and cellulose.

3. A method as claimed in claim 1 wherein the catalyst used is selected from the group consisting of Al-MCM-41, HZSM-5, Hβ, HX, synthetically prepared SAPO-5 and HY.

4. A method as claimed in claim 1 wherein the zeolite used is in its alkali ion form wherein the alkali ion is selected from the group comprising sodium and potassium, ammonium ion form or proton form.

5. A method as claimed in claim 1 wherein the aromatic aldehyde is selected from the group consisting of benzaldehyde, o, m and p-substituted benzaldehydes.

6. A method as claimed in claim 1 wherein the process comprises the in situ synthesis and characterization of meso-tetraphenyl porphyrin of formula 1

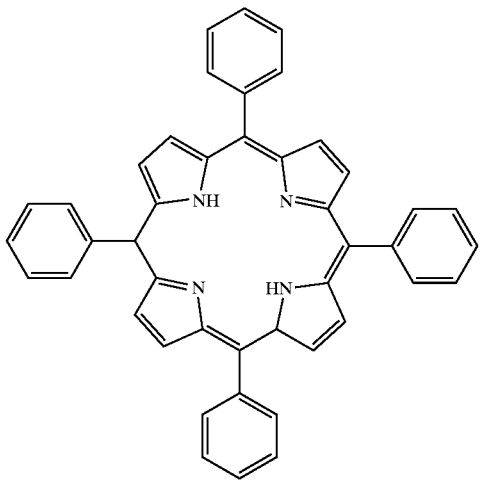

from corresponding pyrrole and benzaldehyde over mesoporous and microporous molecular sieves as stationary phases on inert glass backed supports in a solvent free microwave heating.

7. A method for the high performance Thin Layer Chromatography (TLC) and microwave assisted in-situ synthesis and evaluation of meso-octamethyl calix(4)pyrrole comprising reacting the corresponding pyrrole and ketone over a glass backed zeolite coated TLC plate.

8. A method as claimed in claim 7 wherein the catalyst used is selected from the group consisting of Al-MCM-41, HZSM-5, Hβ, HX, synthetically prepared SAPO-5 and HY.

9. A method as claimed in claim 7 wherein the zeolite used is in its alkali ion form wherein the alkali ion is selected from the group comprising sodium and potassium, ammonium ion form or proton form.

10. A method as claimed in claim 7 wherein the ketone is selected from the group consisting of acetone, methyl ethyl ketone, diethyl ketone, cyclopentanone, cyclohexanone, cycloheptanone, cyclooctanone, cyclododecanone, substituted cyclohexanones, acetophenone and alkyl and aryl derivatives thereof.

11. A method as claimed in claim 7 wherein the zeolite is coated onto the TLC plate using a binder selected from the group consisting of calcium sulfate, gypsum, starch and cellulose.

12. A method as claimed in claim 7 wherein the process comprises the facile and in situ synthesis of a meso-octamethyl calix(4)pyrrole of the formula 2

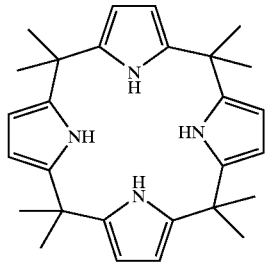

from the corresponding pyrrole and acetone over mesoporous and microporous molecular sieves as stationary phases on inert glass backed supports in a solvent free microwave heating.

* * * * *